United States Patent [19]

Gram et al.

[11] Patent Number: 4,869,112
[45] Date of Patent: Sep. 26, 1989

[54] SCREW-DRIVEN ACTUATOR FOR TEST FRAME

[75] Inventors: Martin M. Gram, St. Louis Park; Richard E. Bearden, Arden Hills, both of Minn.

[73] Assignee: MTS Systems Corporation, Eden Prairie, Minn.

[21] Appl. No.: 268,464

[22] Filed: Nov. 8, 1988

[51] Int. Cl.$^4$ .............................................. G01N 3/08
[52] U.S. Cl. ......................................... 73/856; 73/796
[58] Field of Search ................. 73/856, 796, 826, 827, 73/828, 829, 830, 831, 832, 833, 834

[56] References Cited

U.S. PATENT DOCUMENTS

| | | | |
|---|---|---|---|
| 3,135,106 | 6/1964 | Lazan | 73/796 X |
| 3,203,232 | 8/1965 | Lehnig, Jr. | 73/93 |
| 3,357,755 | 12/1967 | Danly | 308/6 |
| 3,375,709 | 4/1968 | Holmes | 73/93 |
| 3,859,848 | 1/1975 | Dripke | 73/93 |
| 4,096,741 | 6/1978 | Sternstein | 73/90 |
| 4,620,351 | 11/1986 | Teramachi | 29/149.5 R |
| 4,705,491 | 11/1987 | Andersson | 464/167 |

OTHER PUBLICATIONS

Instron Corporation, Catalog page.
Schenk, Catalog page.

*Primary Examiner*—Jerry W. Myracle
*Attorney, Agent, or Firm*—Kinney & Lange

[57] ABSTRACT

A mechanical screw drive loading test frame has a crosshead on the frame with a grip supported from the crosshead, and a second grip for gripping a second end of a specimen on which a second grip is connected to an axially movable shaft which is ragidly supported and guided for axial movement for loading the specimen. The support for the second grip is in a second rigid cross member positioned very close to the second grip to prevent lateral loads from loading the specimen transversly. The loading shaft is loaded from below the rigid cross member by a screw through a coupling and mounting arrangement which isolates load caused by misalignment in the drive screw or drive motor from the movable shaft and second grip.

10 Claims, 3 Drawing Sheets

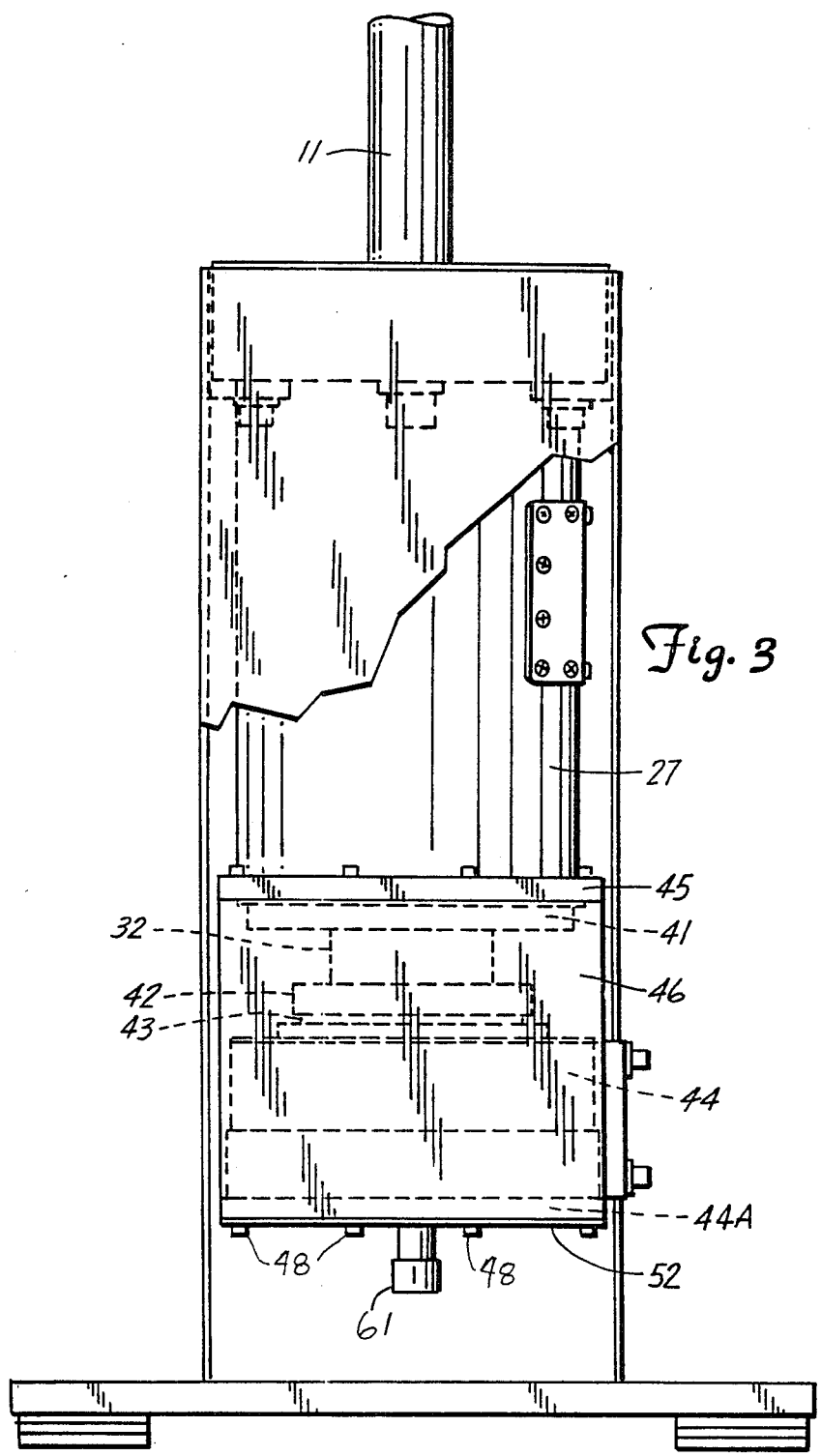

SCREW-DRIVEN ACTUATOR FOR TEST FRAME

BACKGROUND OF THE INVENTION

1. Field of the Invention.

The present invention relates test specimen loading machines that substantially reduce unwanted lateral loads being applied to the specimen while using servo-mechanical loading drives.

2. Description of the Prior Art.

Various screw-driven actuator tension compression test devices have been advanced in the prior art, such as an electro-mechanical actuator for a test frame made by the Instron Corporation, which has a motor mounted below a test frame cross member, and a non-rotating ball screw driven by a rotating nut. A high speed motor is used to drive a gear box through a belt drive and the output of the gear box rotates the nut to load a specimen coupled to the ball screw through a specimen grip. The mounting for the motor requires the use of a torque arm for preventing the motor from rotating when the motor is driving the nut and screw.

Additionally, the Schenck Corporation sells a test frame which utilizes a screw driven actuator with a motor that is mounted below a main base on the test frame, and which uses a frame that is guided on the columns for the test machine to attempt to eliminate side loading of the specimen.

The above described devices require substantial reductions in motor speed using transmissions, and the Schenck device does not provide internal support for the movable loading shaft so that external guiding is required or else side loads on the specimen are present.

A number of patents have also issued for screw actuated test machines, and in particular there are a number of patents which show screws which move and load the main outer columns of test machines. A typical device is shown in U.S. Pat. No. 3,859,848. This test frame utilizes ball screw members for moving a crosshead. The ball screw members form the side support columns.

A ball bearing vertical shaft guide is shown in U.S. Pat. No. 3,357,755, which provides for vertical movement of a shaft as guided by a plurality of balls in an outer housing or race. This guide is for a die-set, and provides a stablized axial guide.

U.S. Pat. No. 3,375,709 shows a loading device which has screw actuated crossheads with edge guides.

U.S. Pat. No. 3,859,848 shows screw actuated crossheads as well with independent supports shown for the loading device for the grips.

U.S. Pat. No. 4,096,741 shows a central load member which is run with a linear motor rather than a screw actuator. A screw is used for taking up slack and providing stop members for a slider.

A sliding spline assembly that slides in a ball bearing housing, which is of the type used for guiding a movable shaft in the present device, is shown in U.S. Pat. No. 4,620,351. The ball-shaft slide assembly that is used for stablizing the loading shaft in the present test machine arrangement is commercially available.

A similar device that provides for nonrotation guiding of a shaft inside a ball housing assembly is shown in U.S. Pat. No. 4,705,491.

U.S. Pat. No. 3,203,232 shows a testing machine with screws at the outer edges of the crosshead used to move the crosshead. This type of mechanical loading device shows ball screws for driving the loading members.

SUMMARY OF THE INVENTION

The present invention relates to a screw-driven actuator for testing specimens in a load frame and which is useful with specimens which are quite brittle, such as ceramic specimens. Lateral loads which cause a ceramic specimen to fracture quite easily are substantially reduced or eliminated.

A specimen is loaded by a pair of grips holding opposite ends of the specimen. One grip is supported from a crosshead mounted on columns relative to a base, and the other grip is moved axially for loading the specimen. The axial movement is generated by a screw-drive assembly mounted below a rigid base cross member. The screw-drive assembly in turn is coupled to provide axial movement to a precisely guided nonrotatable loading shaft which directly supports the second grip. The loading shaft is supported very close to the second grip by a pre-loaded linear bearing that also prevents shaft rotation so that there is little, or no bending of the shaft caused by side loads. The loading shaft is thus precisely axially centered with respect to the upper grip as well.

The loading assembly comprises a drive motor directly coupled to a roller nut driving a roller screw. The screw is coupled to the sliding loading shaft with a rigid coupling. The drive motor outer housing is mounted to the test frame through a flexure plate so that any deflection between the drive motor and the support for the roller nut is accomodated by flexing the mounting plate. The reaction loads on the motor from driving the screw are carried by the flexure plate back to the rigid base member so that no torque arms are used. The motor itself is a low speed (about 66 rpm) motor that is driven without having the need for a gear reduction system.

The roller nut is supported on bearings which tend to isolate any loads from the motor with respect to the axially moving load screw so that all of the parts are very precisely held.

BRIEF DESCRIPTION OF THE DRAWINGS

FIG. 3 is a side view of the test machine of FIG. 1.

DETAILED DESCRIPTION OF THE PREFERRED EMBODIMENTS

Figure 1:
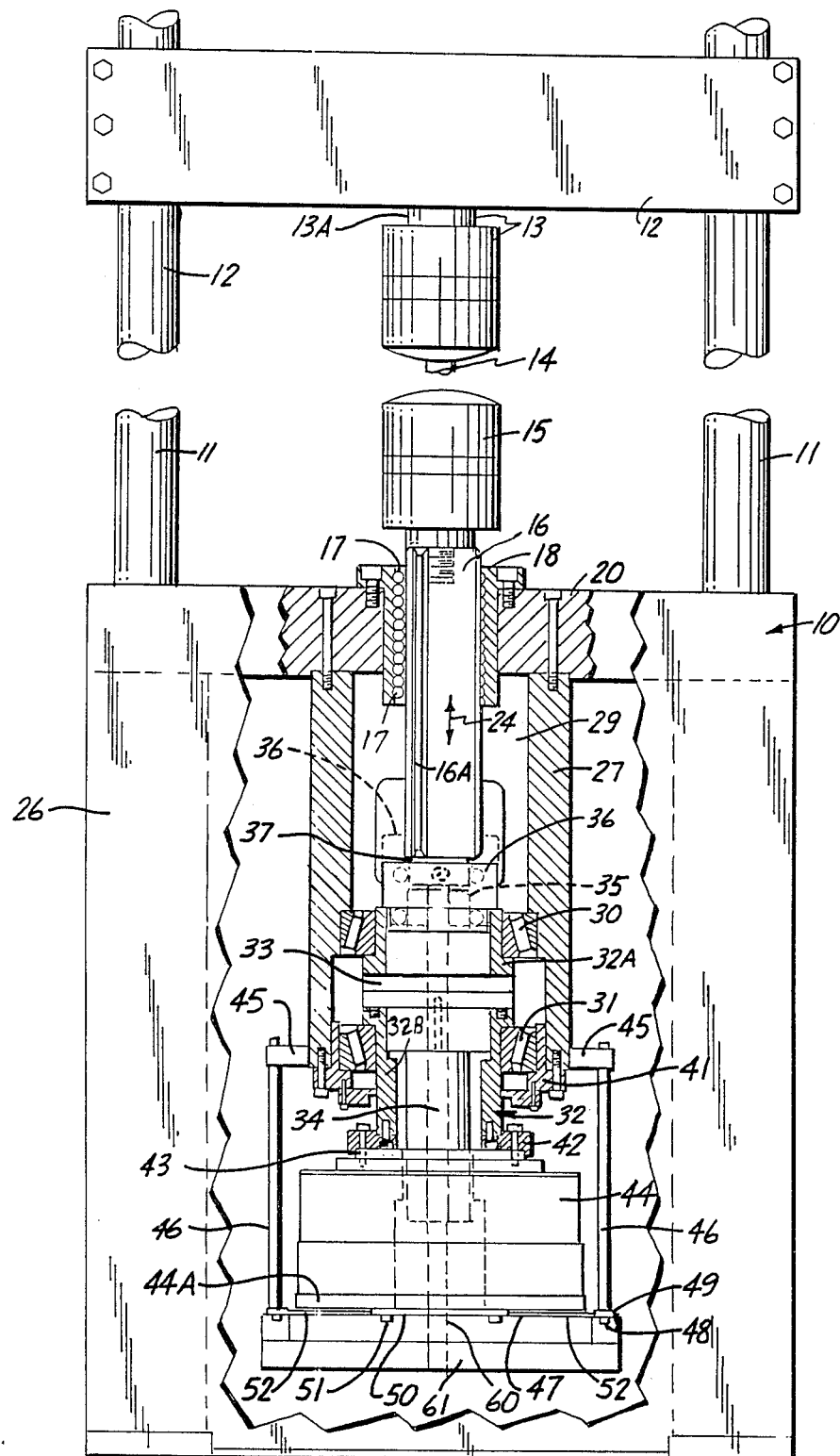
FIG. 1 is an elevational view of a typical test machine utilizing the loading arrangement of the present invention, with parts in section and parts broken away.
Figure 2:
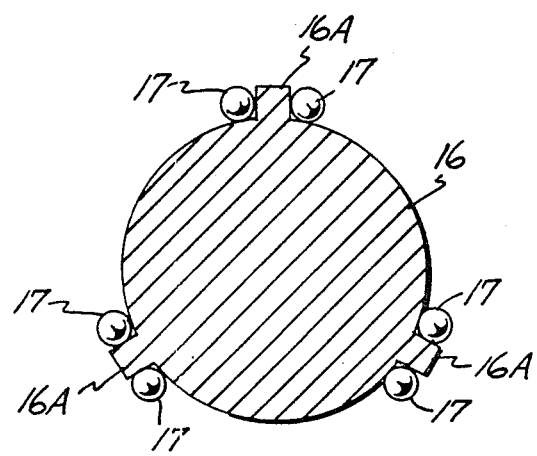
FIG. 2 is a schematic cross section of a guide shaft used for loading the specimen of the present invention.

A specimen testing machine that uses mechanical screw loading for the specimen is shown generally at 10, and includes upright columns 11, (four columns can be used if desired) which extend to support a crosshead 12, which can be fixed in position at a desired vertical location along the columns 11. The crosshead 12 has a grip 13 supported thereon with suitable support comprising a load cell 13A. The grip 13 is a conventional design specimen testing grip that holds an upper end of a brittle specimen 14. The lower end of the specimen 14 is held in a second grip 15, which comprises a lower grip and which is coupled to a vertically sliding, nonrotatable load shaft 16. The load shaft has a number of splines or ribs 16A that extend radially out from the main surface of the shaft. Each of these splines or ribs 16A is precisely held between a series of ball guide members 17, on opposite sides of each individual spline 16A. The ball members 17 are held in an outer race 18 that retains the ball members precisely in position. The outer race 18 is fixed to a very rigid base cross member 20 that forms part of the base 26 of the test frame 10. The rigid base cross member 20 provides a very rigid support for the outer race 18, and thus for the shaft 16, with respect to the columns 11.

A large tubular support housing 27 is attached to the lower side of the base cross member 20, and provides a rigid support depending from the base cross member. Support housing 27 forms a column support that has an interior center opening or passageway 29, and adjacent the lower end thereof there are a pair of vertically spaced bearings 30 and 31 that mount a hub assembly 32 made up of sections 32A and 32B, which in turn is fixed to a nut 33 of a conventional roller screw. A roller screw is substantially similar to what is known as a ball screw, and is a commercially available, low friction fine thread screw. The nut 33 comprises two roller screw nuts loaded back-to-back on a single roller screw member 34 to eliminate axial backlash and the nut is mounted to drive the screw member axially when the nut is rotated. The screw member 34 has an upper end shown generally at 35 in dotted lines that is clamped with a suitable rigid clamp or coupling 36 to an end portion 37 of the load shaft 16. The coupling 36 can be a split clamp used to tightly clamp the screw and shaft together. The shaft 16 cannot rotate so screw 34 does not rotate either.

The screw 34 can be used to move shaft 16 either upwardly or downwardly from a center of travel position. The specimen loading is in either a tension or compression from an initial position of the coupling 36 such as that shown in dotted lines. The nut will move the coupling toward or away from the hub portion 32A. The nut 33 is suitably driven with cap screws from hub portion 32B.

A bearing retainer 41 is connected to the lower end of column 47 and carries a wiper which keeps foreign material from the bearings and the threads of the screw 34 during use.

The hub or housing portion 32B has an outer drive flange 42 mounted on the lower end thereof, and drive flange 42 is in turn coupled to the output drive plate 43 of a high torque, low speed motor 44. The motor 44 has an interior through bore so that the end of the screw 34 will pass through the center of the motor, but is not directly driven by the motor. The motor drive is through the member 43, the flange 42 and the hub 32 to the nut 33. The hub portions 32A and 32B also form bearing sleeves that fit into bearings 30 and 31.

The outer housing of the motor 44 is restrained from rotating, to react the torque applied to the nut 33, through the use of a flexure coupling that permits the motor to deflect vertically when axial loads cause deflection in between the inner and outer uses of bearings 30 and 31. In this form of the invention, the mounting column or sleeve 27 has a pair of side flanges 45, and the flanges 45 have support plates of suitable width and thickness indicated at 46 fixed thereto with suitable cap screws and extending downwardly generally parallel to the axis of the shaft 16 and the screw 34. Plates 46 are to the exterior of the housing for the motor 44, and at the lower end of the plates, which is below the lower end of the motor 44, there is a flexure plate 47 mounted to the support plate.

The flexure plate 47 is a rectangular plate that is fastened to the bottom ends of the support plates 46 with suitable cap screws 48, and which has a center plate portion 50 that is fastened to the housing 44A of the motor 44 with suitable cap screws 51. A rib 49 is on each end of the flexure plate for attachment to the respective support plate 46. The ribs 49 are held with the cap screws 48 and are joined to the center disc 50 through a pair of thin flexure type webs 52 that are integral with the bosses 49 and the center disc 50. The support plates 46, acting through the flanges 45 and the flexure plate 47 restrain the motor from rotating when it is driving the nut 33 and thus is moving the roller screw in one of the directions indicated by the arrow 24. The flexure webs 52 permit the motor 44 to deflect, while keeping it restrained from rotation, so that loads that might be caused by slight misalignments or deflections are not transmitted to the loading shaft 16, and this insures that the loading shaft 16 will be guided in proper position. The guide balls for the ribs or splines 16A insure that there is no rotation or lateral movement of the shaft 16 so that the specimen 14 is not torsionally or laterally loaded.

An LVDT transducer 60 is supported on a cross channel 61 supported below the support plates 46. The LVDT extends through a bore in the roller screw 34 and has its movement sensing rod attached to the shaft 16 with a pin at the end of the shaft 16 to sense axial movement of the roller screw 34, loading shaft 16 and grip 15. This provides a co-axial mounting for the LVDT to provide position sensing that is less sensitive to perturbations, misalignments or deflections of the screw column.

The loading shaft 16 and thus the grip 15 are supported in the lateral direction very close to the base cross member 20. As can be seen, the grip 15 can be threaded to the end of the loading shaft 16 in a conventional manner and tightened down securely so that the end of the grip and the end of the shaft abut under load.

Although the present invention has been described with reference to preferred embodiments, workers skilled in the art will recognize that changes may be made in form and detail without departing from the spirit and scope of the invention.

What is claimed is:

1. In a screw actuated test assembly, a test frame including a base plate member for supporting specimen loading means, said specimen loading means including grip means for attaching to an end of a specimen and applying a load thereto, a shaft slidably mounted for movement relative to said base plate, in directions along the loading axis, said shaft being guided by bearing means through the base member and being restrained from rotation, screw means comprising an outer rotatable nut and an inner screw member extending through the nut, one end of said inner screw member being coupled to said shaft, drive means for said nut comprising a motor coupled to drive said nut, said motor having an outer housing, and flexure means connected between said motor housing and said test frame to restrain the motor housing from rotation and to permit said motor to deflect axially while being restrained from rotation during the driving of said nut.

2. The apparatus as specified in claim 1 wherein the base member comprises a cross member supported above a support surface and a support housing on an opposite side of the base member from the end of the shaft coupled to the grip, an end portion of said housing opposite from said base member having bearing means supported thereon, said nut being mounted in said bearing means for rotation about the same axis as the axis of movement of said shaft.

3. The apparatus as specified in claim 2 wherein said flexure means for supporting said motor is mounted to said support housing at the lower end thereof.

4. The apparatus as specified in claim 2 wherein said bearing means comprise a pair of bearings that securely restrain the nut from axial or lateral movement, and wherein said coupling between said shaft and said screw member is located between the bearing means and the base member.

5. The apparatus as specified in claim 1 wherein said motor has an internal central passageway, and said inner screw member being of size to move axially along the internal central passageway as the screw member is moved by rotation of the nut.

6. The apparatus as specified in claim 1 wherein said means for guiding said shaft as it moves axially comprises a linear ball bearing including a housing mounted on said base member, said shaft having radially extending ribs thereon with balls on opposite sides of said ribs, and said housing retaining said balls for rolling support of said shaft in direction along its axis while restraining rotation thereof.

7. A screw actuator for a test frame having an upper crosshead and a lower base cross member, and grip means on the upper cross member for supporting one end of a specimen to be tested, comprising a shaft slidably mounted for movement relative to said base cross member in direction along a loading axis, coinciding with a longitudinal axis of the shaft, means for guiding said shaft on said base cross member, means for mounting a second grip on a first end of the shaft on a side of the base cross member facing toward the upper cross member, a nut rotatably mounted relative to the base cross member on a side of the base cross member opposite from the means for mounting a second grip, a screw member threadably extending through the nut, one end of said screw member being coupled to an end of said shaft opposite from the first end, and drive means for driving said nut comprising a motor, having an output member coupled to the nut, said motor having an outer housing mounted with respect to the base cross member through a flexure plate which permits said motor to deflect on the longitudinal axis while being restrained from rotation during the driving of said nut.

8. The actuator as specified in claim 7 and a rigid housing mounted to the base cross member on the same side thereof as the nut, said housing forming a wall circumscribing said shaft, and an end portion of said housing opposite from said base cross member having bearing means thereon, said nut being mounted in said bearing means and positioned between the motor and the base cross member.

9. The apparatus as specified in claim 8 wherein said flexure plate has a center portion fixed to said motor and end portions positioned laterally therefrom, the end portions being connected to the center portion by thin flexure plate portions, the end portions being supported relative to the housing.

10. The apparatus as specified in claim 8 wherein said bearing means comprise a pair of bearings spaced in axial direction of the shaft that securely restrain the nut from axial and lateral motion, and a rigid coupling between said shaft and said screw member located between the bearing means and the base cross member.

* * * * *

UNITED STATES PATENT AND TRADEMARK OFFICE
CERTIFICATE OF CORRECTION

PATENT NO. : 4,869,112

DATED : September 26, 1989

INVENTOR(S) : Martin M. Gram et al.

It is certified that error appears in the above-identified patent and that said Letters Patent is hereby corrected as shown below:

Title page:

In the Abstract, line 5, delete "ragidly" and insert --rigidly--.

In the Abstract, line 10, delete "transversly" and insert --transversely--.

Signed and Sealed this

Thirtieth Day of October, 1990

Attest:

HARRY F. MANBECK, JR.

Attesting Officer

Commissioner of Patents and Trademarks